(12) United States Patent
Miyazaki et al.

(10) Patent No.: US 7,803,953 B2
(45) Date of Patent: Sep. 28, 2010

(54) CATALYST FOR PRODUCING ARYLAMINE AND PROCESS FOR PRODUCING ARYLAMINE BY MEANS THEREOF

(75) Inventors: Takanori Miyazaki, Shunan (JP); Masakazu Nishiyama, Shunan (JP); Naoki Matsumoto, Shunan (JP)

(73) Assignee: Tosoh Corporation, Shunan-shi, Yamaguchi-ken (JP)

(*) Notice: Subject to any disclaimer, the term of this patent is extended or adjusted under 35 U.S.C. 154(b) by 4 days.

(21) Appl. No.: 11/806,565

(22) Filed: Jun. 1, 2007

(65) Prior Publication Data
US 2007/0282111 A1    Dec. 6, 2007

(30) Foreign Application Priority Data
Jun. 6, 2006    (JP) .............................. 2006-156919

(51) Int. Cl.
*C07C 209/10*    (2006.01)

(52) U.S. Cl. ................... 548/444; 548/469; 548/373.1; 564/395; 564/405; 564/305

(58) Field of Classification Search ....................... None
See application file for complete search history.

(56) References Cited

U.S. PATENT DOCUMENTS

| | | | |
|---|---|---|---|
| 5,502,183 A * | 3/1996 | Andrews et al. ............... 540/46 |
| 5,929,281 A | 7/1999 | Nishiyama et al. |
| 6,251,947 B1 | 6/2001 | Basarab et al. |
| 6,410,732 B2 * | 6/2002 | Akhavan-Tafti et al. ...... 546/102 |
| 6,455,720 B1 * | 9/2002 | Suzuki et al. .................. 556/21 |
| 6,518,444 B1 * | 2/2003 | McConville et al. ........... 556/52 |
| 6,642,392 B1 | 11/2003 | Basarab et al. |
| 6,759,429 B2 * | 7/2004 | Tokunaga et al. ............ 514/423 |
| 6,759,554 B2 * | 7/2004 | Buchwald et al. ............ 564/192 |
| 6,818,368 B2 * | 11/2004 | Tanaka et al. ................. 430/73 |
| 6,958,204 B2 * | 10/2005 | Tanaka et al. ................ 430/133 |
| 7,238,763 B2 * | 7/2007 | Nishikubo et al. ........... 526/328 |
| 7,250,532 B2 * | 7/2007 | Iwakuma et al. ............. 564/307 |
| 7,321,066 B2 * | 1/2008 | Kawamura et al. ........... 564/385 |
| 2003/0181496 A1 * | 9/2003 | Tokunaga et al. ............ 514/372 |
| 2006/0025472 A1 | 2/2006 | Basarab et al. |
| 2006/0178425 A1 | 8/2006 | Basarab et al. |
| 2007/0027299 A1 * | 2/2007 | Morishita et al. ............ 528/423 |
| 2007/0073086 A1 | 3/2007 | Mathiaparanam |
| 2007/0287821 A1 * | 12/2007 | Doetz et al. .................... 528/8 |

FOREIGN PATENT DOCUMENTS

| | | | |
|---|---|---|---|
| JP | 03284653 A | * | 12/1991 |
| JP | 03284654 A | * | 12/1991 |
| JP | 08-048974 | | 2/1996 |
| JP | 10-139742 | | 5/1998 |
| JP | 2000336045 A | * | 12/2000 |
| JP | 2001-011046 | | 1/2001 |
| WO | WO 98/33765 A | | 8/1998 |
| WO | WO 2004/092245 A | | 11/2004 |

OTHER PUBLICATIONS

Shirota et al.: "Starburst Molecules for Amorphous Molecular Materials," The Chemical Society of Japan, Chemistry Letters, pp. 1145-1148, 1989.
Guram et al.: "A Simple Catalytic Method for the Conversion of Aryl Bromides to Arlamines," VCH Verlagsgesellschaft mbH, D-69451, vol. 34, No. 12, pp. 1348-1350, Weinheim, 1995.
Wolfe et al.: "An Improved Catalyst System for Aromatic Carbon-Nitrogen Bond Formation: The Possible Involvement of Bis(Phosphine) Palladium Complexes as Key Intermediates," J.Am. Chem. Soc., pp. 7215-7216, 1996.
Wolfe et al.: "Palladium-Catalyzed Amination of Aryl Iodides," J.Org. Chem., pp. 1133-1135, 1996.
Kuwano et al, "Aqueous Hydroxide as a Base for Palladium-Catalyzed Amination of Aryl . . . ", Journal of Organic Chemistry, American Chemical Society, Easton, U.S., vol. 67, No. 18, 2002, pp. 6479-6486; XP002366816.

* cited by examiner

*Primary Examiner*—Daniel M Sullivan
*Assistant Examiner*—Yevegeny Valenrod
(74) *Attorney, Agent, or Firm*—Nixon & Vanderhye P.C.

(57) ABSTRACT

To provide a process for preparing an arylamine highly selectively and highly efficiently, which is also industrially superior without a fear of a side reaction when a strong base is employed. An aryl compound having an active group is reacted with an amine compound in the presence of a base by means of a catalyst for producing an arylamine which comprises a palladium compound having a tertiary phosphine group and a phase-transfer catalyst.

3 Claims, No Drawings

CATALYST FOR PRODUCING ARYLAMINE AND PROCESS FOR PRODUCING ARYLAMINE BY MEANS THEREOF

This application claims priority to JP 2006-156919 filed 6 Jun. 6, 2006, the entire contents of which are hereby incorporated herein by reference.

The present invention relates to a process for producing an arylamine highly selectively and highly efficiently wherein an inexpensive base is employed.

Aryl amines are a group of compounds useful as materials for pharmaceuticals and agricultural chemicals and for electronic materials, and it has been known since long ago that such a group of compounds can be prepared by a Ullmann method employing a copper catalyst (e.g. Patent Document 1 and Non-Patent Document 1). Further, in recent years, it has been reported that a wide range of arylamines can easily be prepared from an amine compound and an aryl halide by a combination of a palladium catalyst with a proper ligand and tert-BuONa as a strong base (e.g. Patent Document 2 and Non-Patent Documents 2 to 4). Further, an N-arylation reaction of a cyclic conjugated amine has been reported wherein a weak base such as potassium carbonate is used as a base, and a catalyst system comprising tri-tert-butylphosphine and palladium is used (e.g. Patent Document 3).

Patent Document 1: JP-A-8-48974
Patent Document 2: JP-A-10-139742
Patent Document 3: JP-A-2001-11046
Non-Patent Document 1: Chem. Lett., pp. 1145-1148 (1989)
Non-Patent Document 2: Angew. Chem. Int. Ed. Engl., 34, No. 12, 1348 (1995)
Non-Patent Document 3: J. Am. Chem. Soc., 118, 7215 (1996)
Non-Patent Document 4: J. Org. Chem., 61, 1133 (1996)

However, the Ullmann method required a high temperature of at least 150° C. and a long reaction time, and the reactivity was low, and the yield of the desired arylamines was not satisfactory. Further, a large amount of a copper catalyst was required, whereby such a method was problematic also from the viewpoint of the environmental problem. In the method of combining a palladium catalyst with a proper ligand and tert-BuONa as a strong base, the reactivity was sufficiently improved as compared with the Ullmann method, but a strong base was essential, whereby there was a problem that the method was hardly applicable to an N-arylation reaction of an amine compound having a relatively low pKa value of N—H proton like a carbazole.

Namely, in an N-arylation reaction represented by a carbazole, if a strong base such as tert-BuONa is employed, sodium amide which is inert to the reaction will readily be formed, and therefore there is a restriction such that a weak base represented by potassium carbonate has to be used. In an N-arylation reaction employing such a weak base, the reactivity will be substantially influenced by the aryl compound having an active group or the amine compound, to be used, and there has been no established reaction conditions. In JP-A-2001-11046, an N-arylation reaction of a carbazole is reported. However, in some cases, it was essential to use an expensive base such as rubidium carbonate in order to increase the reactivity, and three equivalents of a carbazole to the aryl halide is employed, whereby there was a problem that the reactivity was inadequate, and the method was not economical.

It is an object of the present invention to provide a process for producing an arylamine, which is carried out under a mild condition employing an inexpensive inorganic base and which is extremely effective in an N-arylation reaction of a wide range of amine compounds, particularly in an N-arylation reaction of an amine compound having a relatively low pKa value like a carbazole.

The present inventors have conducted an extensive study to solve the above-mentioned problems and as a result, have found it possible to prepare an arylamine highly selectively and highly efficiently in the presence of an inexpensive base by using a catalyst system comprising a palladium compound having a tertiary phosphine group and a phase-transfer catalyst. Thus, the present invention has been accomplished.

Namely, the present invention provides a catalyst for producing an arylamine, which comprises a palladium compound having a tertiary phosphine group and a phase-transfer catalyst, and a novel process for producing an arylamine by means of such a catalyst.

Now, the present invention will be described in detail with reference to the preferred embodiments.

The aryl compound having an active group to be used in the present invention is specifically a compound represented by the following formula (I):

$$\text{Ar}-(-X)_n \qquad (I)$$

wherein X is a triflate, iodide, bromide or chloride, and n is an integer of from 1 to 4. Ar is a $C_{6-40}$ aryl group or $C_{3-40}$ heteroaryl group, which may have a substituent.

A specific example of the Ar group is not particularly limited, but may, for example, be an aryl group such as a phenyl group, a naphthyl group, an anthracenyl group, a biphenyl group, a terphenyl group, an indenyl group, a fluorenyl group, a fluorenonyl group or a pyranyl group, or a heteroaryl group such as a pyridinyl group, a pyradinyl group, a quinolyl group, an isoquinolyl group, a furanyl group, a benzofuranyl group, a thiophenyl group, a benzothiophenyl group, a pyrrolyl group, an indolyl group or a carbazoyl group.

The amine compound to be used in the present invention may be a primary amine or a secondary amine. The primary amine is not particularly limited, but may, for example, be an aliphatic primary amine such as ethylamine, propylamine, butylamine, pentylamine or octylamine, or an aromatic primary amine such as aniline, 2-naphthylamine, 2-aminobiphenyl or 4-aminobiphenyl, which may have a substituent on the aromatic ring. The secondary amine is not particularly limited, but may, for example, be an alicyclic secondary amine such as piperazine, 2-methylpiperazine, N-methylpiperazine, N-benzylpiperazine, piperidine, 2-ethylpiperidine or pyrrolidine, an aliphatic secondary amine such as dimethylamine or diethylamine, an aromatic secondary amine such as N-methylaniline, N-ethylaniline, N-ethylbenzylamine or diphenylamine, which may have a substituent on the aromatic ring, or an aromatic cyclic amine compound such as a carbazole, an indole, a pyrrole, a pyrazole, an imidazole, an indazole, or a benzimidazole. A specific example of the carbazole may, for example, be carbazole, 2-methylcarbazole or 2-methoxycarbazole. A specific example of the indole may, for example, be indole, 2-methylindole, 3-methylindole, 4-methylindole, 5-methylindole, 2-phenylindole or 5-methoxyindole. A specific example of the pyrrole may, for example, be pyrrole, 2-methylpyrrole, 2-acetylpyrrole or 2-dimethylaminopyrrole. A specific example of the pyrazole may, for example, be pyrazole, 3-methylpyrazole, 3,5-dimethylpyrazole, 3-phenylpyrazole or 3,5-diphenylpyrazole. A specific example of the imidazole may, for example, be imidazole, 2-methylimidazole, 4-methylimidazole, 2,4-dimethylimidazole, 2-phenylimidazole or 4-phenylimidazole. A specific example of the indazole may, for example, be indazole, 5-methylindazole or 5-dimethylaminoindazole. A specific example of the benzimidazole may, for example, be benzimidazole, 2-methylbenzimidazole, 5,6-dimethylbenzimidazole, 5-methoxybenzimidazole or 2-phenylbenzimidazole.

In the present invention, the amount of the amine compound to be added, is not particularly limited, but it is usually within a range of from 0.5 to 8 times by mol to the aryl compound having an active group, preferably within a range of from 0.8 to 4 times by mol, from the viewpoint of the economical efficiency and purification efficiency after the reaction.

In the present invention, a catalyst system comprising a palladium compound having a tertiary phosphine group and a phase-transfer catalyst, is used. The palladium compound is not particularly limited, but may, for example, be a tetravalent palladium compound such as sodium hexachloropalladium (IV) acid tetrahydrate or potassium hexachloropalladium(IV) acid, a bivalent palladium compound such as palladium(II) chloride, palladium(II) bromide, palladium(II) acetate, palladium(II) acetylacetonate, palladium(II) dichlorobis(benzonitrile), palladium(II) dichlorobis(acetonitrile), palladium(II) dichlorobis(triphenylphosphine), palladium(II) dichlorotetraammine, palladium(II) dichloro(cycloocta-1,5-diene) or palladium(II) trifluoroacetate, or a zero valent palladium compound such as dipalladium(0) tris(dibenzylideneacetone), dipalladium(0) tris(dibenzylideneacetone) chloroform complex, or palladium(0) tetrakis(triphenylphosphine).

Such palladium compounds may be used alone or in combination as a mixture of two or more of them.

In the present invention, the amount of the palladium compound to be used is not particularly limited, but usually within a range of from 0.00001 to 20 mol %, as calculated as palladium, per mol of the aryl compound having an active group. When the palladium compound is within the above range, the arylamine can be prepared with a high selectivity, but with a view to further improving the activity or to use an expensive palladium compound properly, a more preferred amount of the palladium compound to be used is within a range of from 0.001 to 5 mol %, as calculated as palladium, per mol of the aryl compound having an active group.

In the present invention, the tertiary phosphine to be used in combination with the palladium compound is not particularly limited, but it may, for example, be a monodentate phosphine such as triethylphosphine, tricyclohexylphosphine, triisopropylphosphine, tri-n-butylphosphine, tri-iso-butylphosphine, tri-sec-butylphosphine, tri-tert-butylphosphine, triphenylphosphine, tri-pentafluorophenylphosphine, tri-o-tolylphosphine, tri-m-tolylphosphine, tri-p-tolylphosphine, tri(2,6-dimethylphenoxy)phosphine, tri(2-tert-butylphenoxy)phosphine, triphenoxyphosphine, tri(4-methylphenoxy)phosphine, tri(2-methylphenoxy)phosphine, 2-(dicyclohexylphosphino)biphenyl or (2-cyclohexylphenyl)di-tert-butylphosphine, or a bidentate phosphine such as 1,2-bis (diphenylphosphino)benzene, 2,2'-bis(diphenylphosphino)-1,1'-binaphthyl, 1,2-bis(diphenylphosphino)ethane, 1,3-bis (diphenylphosphino)propane or 1,1-(diphenylphosphino) ferrocene. Among them, tri-tert-butylphosphine is more preferred in order to improve the selectivity for an arylamine.

Such tertiary phosphines may be used alone or in combination as a mixture of two or more of them.

In the present invention, the amount of the tertiary phosphine to be used is usually within a range of from 0.01 to 10,000 times by mol to the palladium compound. When the amount of the tertiary phosphine to be used is within the above range, there will be no change in the selectivity for the arylamine. In order to further improve the activity or to use the expensive tertiary phosphine properly, a more preferred amount of the tertiary phosphine to be used is within a range of from 0.1 to 10 times by mol to the palladium compound.

In the present invention, the palladium compound and the tertiary phosphine are essential, and both are combined to be a catalyst, which is added to the reaction system. As the addition method, they may be independently added to the reaction system, or they may be preliminarily formulated in the form of a complex, which may be added.

In the present invention, a phase-transfer catalyst is used. Such a phase-transfer catalyst is not particularly limited, but specifically, it may, for example, be a crown ether such as 24-crown-8, 18-crown-6, 15-crown-5, 12-crown-4, benzo-18-crown-6, benzo-15-crown-5, benzo-12-crown-4, dibenzo-30-crown-10, dibenzo-24-crown-8, dibenzo-21-crown-7, dibenzo-18-crown-6, dicyclohexano-24-crown-8, dicyclohexano-18-crown-6, N,N'-dibenzyl-4, or 13-diaza-18-crown-6, or a quaternary ammonium salt such as tetra(n-butyl)ammonium chloride, tetra(n-butyl)ammonium bromide, benzyltriethylammonium chloride, triethyl-n-dodecylammonium chloride, triethyl-n-dodecylammonium bromide, trimethyl-n-hexadecylammonium chloride, or trimethyl-n-hexadecylammonium bromide. Among them, preferred from the viewpoint of the reactivity is a crown ether, and from the viewpoint of the reactivity and economical efficiency, more preferred is 18-crown-6.

Such phase-transfer catalysts may be used alone or in combination as a mixture of two or more of them.

In the present invention, the amount of the phase-transfer catalyst is usually within a range of from 0.5 to 20 times by mol, more preferably within a range of from 1 to 10 times by mol, to the palladium compound.

The present catalyst is effective particularly for a reaction of an aryl compound having an active group with the above-mentioned aromatic cyclic amine compound.

In the present invention, an inorganic base is preferably used as the base. The inorganic base is not particularly limited, but specifically, it may, for example, be an alkali metal salt such as lithium carbonate, sodium carbonate, potassium carbonate, rubidium carbonate, cesium carbonate, sodium hydrogencarbonate, potassium hydrogencarbonate, rubidium hydrogencarbonate or potassium phosphate; or an alkaline earth metal salt such as magnesium carbonate or calcium carbonate. Among them, particularly preferred from the viewpoint of the economical efficiency is potassium carbonate.

In the present invention, the amount of the base to be used is usually within a range of from 0.8 to 8 times by mol, preferably within a range of from 1 to 4 times by mol, to the aryl compound having an active group.

The amination reaction in the present invention is carried out usually in the presence of an inert solvent. Such an inert solvent is not particularly limited so long as it is a solvent not to substantially impair the present reaction. Specifically, an aromatic hydrocarbon solvent such as benzene, toluene, xylene or mesitylene, may be preferably employed.

The process of the present invention is preferably carried out under normal pressure in an atmosphere of an inert gas such as nitrogen or argon, but it may be carried out under a pressurized condition.

In the present invention, the reaction temperature may be within a range of from 20 to 300° C., more preferably within a range of from 50 to 200° C., further preferably within a range of from 60 to 160° C.

According to the present invention, by using a crown ether as a phase-transfer catalyst, an arylamine may be prepared highly selectively and highly efficiently in the presence of an inexpensive base. Further, there is no fear of a side reaction at the time of employing a strong base, whereby it is possible to present a process which is superior also industrially.

Now, the present invention will be described with reference to Examples. However, it should be understood that the present invention is by no means restricted to such Examples. The results of reactions by combinations of substrates are shown in Tables 1 and 2.

Further, the gas chromatography quantitative analyses were carried out by using GC-17A, manufactured by Shimadzu Corporation, a capillary column (NB-5, manufactured by GL Sciences Company) and a detector (FID) under a temperature-raising condition of 8° C./min from 100° C. to 300° C.

EXAMPLE 1

Into a 10 mL Schrenk tube, a stirrer was put, and the tube was flushed with nitrogen. Then, 45 mg (0.049 mmol) of dipalladium(0) tris(dibenzylideneacetone), 66 mg (0.32 mmol) of tri-tert-butylphosphine and 1 mL of o-xylene were added, and this solution was stirred for 20 minutes at 60° C. in a nitrogen atmosphere to obtain a catalyst solution. A 100 mL three necked round bottomed flask was flushed with nitrogen, 0.79 g (5.0 mmol) of bromobenzene, 1.66 g (9.9 mmol) of carbazole, 1.37 g (9.9 mmol) of potassium carbonate, 39 mg (0.15 mmol) of 18-crown-6 and 30 mL of o-xylene were added. At room temperature, to this solution, the previous catalyst solution was added by a syringe, and the reaction solution was heated to 120° C. Two hours later, the heating was terminated, and the reaction solution was left to cool to room temperature. This reaction solution was extracted with 100 g of toluene, and the obtained organic layer was dried over anhydrous magnesium sulfate. This organic layer was subjected to a gas chromatography quantitative analysis using triphenylamine as an internal standard substance, whereby N-phenyl carbazole was 1.21 g (yield: 99%).

EXAMPLE 2

Into a 10 mL Schrenk tube, a stirrer was put, and the tube was flushed with nitrogen. Then, 45 mg (0.049 mmol) of dipalladium(0) tris(dibenzylideneacetone), 66 mg (0.32 mmol) of tri-tert-butylphosphine and 1 mL of o-xylene were added, and this solution was stirred for 20 minutes at 60° C. in a nitrogen atmosphere to obtain a catalyst solution. A 100 mL three necked round bottomed flask was flushed with nitrogen, and 1.00 g (5.0 mmol) of p-bromonitrobenzene, 1.66 g (9.9 mmol) of carbazole, 1.37 g (9.9 mmol) of potassium carbonate, 39 mg (0.15 mmol) of 18-crown-6 and 30 mL of o-xylene were added. At room temperature, to this solution, the previous catalyst solution was added by a syringe, and the reaction solution was heated to 120° C. Seven hours later, the heating was terminated, and the reaction solution was left to cool to room temperature. This reaction solution was extracted with 100 g of toluene, and the obtained organic layer was dried over anhydrous magnesium sulfate. This organic layer was subjected to a gas chromatography quantitative analysis using triphenylamine as an internal standard substance, whereby N-(4-nitrophenyl)carbazole was 1.14 g (yield: 80%).

EXAMPLE 3

Into a 10 mL Schrenk tube, a stirrer was put, and the tube was flushed with nitrogen. Then, 45 mg (0.049 mmol) of dipalladium(0) tris(dibenzylideneacetone), 66 mg (0.32 mmol) of tri-tert-butylphosphine and 1 mL of o-xylene were added, and this solution was stirred for 20 minutes at 60° C. in a nitrogen atmosphere to obtain a catalyst solution. A 100 mL three necked round bottomed flask was flushed with nitrogen, and 0.94 g (5.0 mmol) of p-bromoanisole, 1.66 g (9.9 mmol) of carbazole, 1.37 g (9.9 mmol) of potassium carbonate, 39 mg (0.15 mmol) of 18-crown-6 and 30 mL of o-xylene were added. At room temperature, to this solution, the previous catalyst solution was added by a syringe, and the reaction solution was heated to 120° C. Five hours later, the heating was terminated, and the reaction solution was left to cool to room temperature. This reaction solution was extracted with 100 g of toluene, and the obtained organic layer was dried over anhydrous magnesium sulfate. This organic layer was subjected to a gas chromatography quantitative analysis using triphenylamine as an internal standard substance, whereby N-(4-methoxyphenyl)carbazole was 0.87 g (yield: 71%).

EXAMPLE 4

Into a 10 mL Schrenk tube, a stirrer was put, and the tube was flushed with nitrogen. Then, 45 mg (0.049 mmol) of dipalladium(0) tris(dibenzylideneacetone), 66 mg (0.32 mmol) of tri-tert-butylphosphine and 1 mL of benzene were added, and this solution was stirred for 20 minutes at 60° C. in a nitrogen atmosphere to obtain a catalyst solution. A 100 mL three necked round bottomed flask was flushed with nitrogen, and 1.08 g (5.0 mmol) of methyl 4-bromobenzoate, 1.66 g (9.9 mmol) of carbazole, 1.37 g (9.9 mmol) of potassium carbonate, 39 mg (0.15 mmol) of 18-crown-6 and 30 mL of benzene were added. At room temperature, to this solution, the previous catalyst solution was added by a syringe, and the reaction solution was heated to 90° C. Seven hours later, the heating was terminated, and the reaction solution was left to cool to room temperature. This reaction solution was extracted with 100 g of toluene, and the obtained organic layer was dried over anhydrous magnesium sulfate. This organic layer was subjected to a gas chromatography quantitative analysis using triphenylamine as an internal standard substance, whereby N-(4-methyl benzoate)carbazole was 1.50 g (yield: 99%).

COMPARATIVE EXAMPLE 1

The same operation as in Example 1 was carried out except that no 18-crown-6 was added, whereby 0.34 g (yield: 28%) of N-phenylcarbazole was obtained.

COMPARATIVE EXAMPLE 2

The same operation as in Example 1 was carried out except that no 18-crown-6 was added, and the reaction time was changed to 31 hours, whereby 0.90 g (yield: 74%) of N-phenylcarbazole was obtained.

COMPARATIVE EXAMPLE 3

The same operation as in Example 2 was carried out except that no 18-crown-6 was added, whereby 0.20 g (yield: 14%) of N-(4-nitrophenyl)carbazole was obtained.

COMPARATIVE EXAMPLE 4

The same operation as in Example 2 was carried out except that no 18-crown-6 was added, and the reaction time was changed to 28 hours, whereby 0.65 g (yield: 45%) of N-(4-nitrophenyl)carbazole was obtained.

COMPARATIVE EXAMPLE 5

The same operation as in Example 3 was carried out except that no 18-crown-6 was added, whereby 0.23 g (yield: 19%) of N-(4-methoxyphenyl)carbazole was obtained.

COMPARATIVE EXAMPLE 6

The same operation as in Example 3 was carried out except that no 18-crown-6 was added, and the reaction time was changed to 31 hours, whereby 0.43 g (yield: 31%) of N-(4-methoxyphenyl)carbazole was obtained.

COMPARATIVE EXAMPLE 7

The same operation as in Example 4 was carried out except that no 18-crown-6 was added, whereby 0.47 g (yield: 31%) of N-(4-methyl benzoate)carbazole was obtained.

COMPARATIVE EXAMPLE 8

The same operation as in Example 4 was carried out except that no 18-crown-6 was added, and the reaction time was changed to 22 hours, whereby 0.83 g (yield: 55%) of N-(4-methyl benzoate)carbazole was obtained.

TABLE 1

| | Amine compound | Ar—X | Product | Reaction time (hr) | Yield (%) |
|---|---|---|---|---|---|
| Ex. 1 | carbazole | PhBr | N-phenylcarbazole | 2 | 99 |
| Comp. Ex. 1 | | | | 2 | 28 |
| Comp. Ex. 2 | | | | 31 | 74 |
| Ex. 2 | carbazole | 4-bromonitrobenzene | N-(4-nitrophenyl)carbazole | 7 | 80 |
| Comp. Ex. 3 | | | | 7 | 14 |
| Comp. Ex. 4 | | | | 28 | 45 |

TABLE 1-continued

| | Amine compound | Ar—X | Product | Reaction time (hr) | Yield (%) |
|---|---|---|---|---|---|
| Ex. 3 | carbazole | 4-bromoanisole | 9-(4-methoxyphenyl)carbazole | 5 | 71 |
| Comp. Ex. 5 | | | | 5 | 19 |
| Comp. Ex. 6 | | | | 31 | 31 |
| Ex. 4 | carbazole | methyl 4-bromobenzoate | methyl 4-(carbazol-9-yl)benzoate | 7 | 99 |
| Comp. Ex. 7 | | | | 7 | 31 |
| Comp. Ex. 8 | | | | 22 | 55 |

EXAMPLE 5

Into a 10 mL Schrenk tube, a stirrer was put, and the tube was flushed with nitrogen. Then, 45 mg (0.049 mmol) of dipalladium(0) tris(dibenzylideneacetone), 66 mg (0.32 mmol) of tri-tert-butylphosphine and 1 mL of o-xylene were added, and this solution was stirred for 20 minutes at 60° C. in a nitrogen atmosphere to obtain a catalyst solution. A 100 mL three necked round bottomed flask was flushed with nitrogen, and 0.79 g (5.0 mmol) of bromobenzene, 1.69 g (10.0 mmol) of diphenylamine, 2.12 g (10.0 mmol) of potassium phosphate, 39 mg (0.15 mmol) of 18-crown-6 and 30 mL of o-xylene were added. At room temperature, to this solution, the previous catalyst solution was added by a syringe, and the reaction solution was heated to 120° C. Ten hours later, the heating was terminated, and the reaction solution was left to cool to room temperature. This reaction solution was extracted with 100 g of toluene, and the obtained organic layer was dried over anhydrous magnesium sulfate. This organic layer was subjected to a gas chromatography quantitative analysis using 2-bromonaphthalene as an internal standard substance, whereby triphenylamine was 0.86 g (yield: 70%).

COMPARATIVE EXAMPLE 9

The same operation as in Example 5 was carried out except that no 18-crown-6 was added, whereby 0.25 g (yield: 20%) of triphenylamine was obtained.

COMPARATIVE EXAMPLE 10

The same operation as in Example 5 was carried out except that no 18-crown-6 was added, and the reaction time was changed to 23 hours, whereby 0.66 g (yield: 54%) of triphenylamine was obtained.

TABLE 2

| | Amine compound | Ar—X | Product | Reaction time (hr) | Yield (%) |
|---|---|---|---|---|---|
| Ex. 5 | (diphenylamine structure) | (bromobenzene structure) | (triphenylamine structure) | 10 | 70 |
| Comp. Ex. 9 | | | | 10 | 20 |
| Comp. Ex. 10 | | | | 23 | 54 |

The entire disclosure of Japanese Patent Application No. 2006-156919 filed on Jun. 6, 2006 including specification, claims and summary is incorporated herein by reference in its entirety.

What is claimed is:

1. A process for producing an arylamine, which comprises reacting an aryl compound having an active group with an amine compound in the presence of a catalyst for producing an arylamine which comprises a palladium compound having a tertiary phosphine group; a crown ether compound; and a base which is selected from lithium carbonate, sodium carbonate, potassium carbonate, rubidium carbonate, cesium carbonate, sodium hydrogencarbonate, potassium hydrogencarbonate, rubidium hydrogencarbonate, potassium phosphate, magnesium carbonate or calcium carbonate.

2. The process for producing an arylamine according to claim 1, wherein the active group is a triflate or a halogen atom.

3. A process for producing an arylamine, which comprises reacting an aryl compound having an active group with an amine compound selected from the group consisting of carbazoles, pyrroles, indoles and imidazoles in the presence of a catalyst for producing an arylamine which comprises a palladium compound having a tertiary phosphine group; a crown ether compound; and a base which is selected from lithium carbonate, sodium carbonate, potassium carbonate, rubidium carbonate, cesium carbonate, sodium hydrogencarbonate, potassium hydrogencarbonate, rubidium hydrogencarbonate, potassium phosphate, magnesium carbonate or calcium carbonate.

* * * * *